United States Patent [19]

Suzuki et al.

[11] Patent Number: 5,591,813
[45] Date of Patent: Jan. 7, 1997

[54] AMIDE GROUP-CONTAINING DIISOCYANATES AND AMIDE GROUP-CONTAINING EPOXY RESINS

[75] Inventors: Kenji Suzuki, Hitachi; Yoshiyuki Mukoyama, Chiba; Toshihiko Ito, Ibaraki-ken, all of Japan

[73] Assignee: Hitachi Chemical Company, Ltd., Tokyo, Japan

[21] Appl. No.: 470,630

[22] Filed: Jun. 6, 1995

Related U.S. Application Data

[62] Division of Ser. No. 245,671, May 18, 1994.

[30] Foreign Application Priority Data

May 21, 1993 [JP] Japan ............................ 5-119702
Dec. 13, 1993 [JP] Japan ............................ 5-311662

[51] Int. Cl.$^6$ ............................ C08G 18/28; C08G 18/77
[52] U.S. Cl. ............................ 525/528; 528/73
[58] Field of Search ............................ 525/528; 528/73

[56] References Cited

U.S. PATENT DOCUMENTS 3,334,110 8/1967 Schramm ............................ 260/307
3,383,400 5/1968 Meisert et al. ............................ 260/453

FOREIGN PATENT DOCUMENTS 0296450 12/1988 European Pat. Off. .

OTHER PUBLICATIONS

Proc. SPI Annu. Tech./Mark Conf. (1982), 27th (Meet. Minds: Mark. Polyurethane Technol.), 58–65 Arendt et al.
Journal of Applied Polymer Science, vol. 40, pp. 1433–1443 (1990).

*Primary Examiner*—Frederick Krass
*Attorney, Agent, or Firm*—Antonelli, Terry, Stout & Kraus

[57] ABSTRACT

An amide group-containing epoxy resin obtained by reacting an epoxy resin with an amide group-containing diisocyanate obtained by reacting a diisocyanate with a dicarboxylic acid gives a uniform cured article showing high adhesiveness and is usable as an adhesive, a coating composition, and the like.

11 Claims, 6 Drawing Sheets

AMIDE GROUP-CONTAINING DIISOCYANATES AND AMIDE GROUP-CONTAINING EPOXY RESINS

This application is a Divisional application of application Ser. No. 245,671, filed May 18, 1994.

BACKGROUND OF THE INVENTION

This invention relates to an amide group-containing diisocyanate compound, a process for producing the same, an amide group-containing epoxy resin, and a process for producing the same.

It has been known that since polyamide resins have amide bonds wherein nitrogen atom and a carbon atom are bound with high polarity, a strong hydrogen bond and a large bond energy, these resins are excellent in heat resistance but low in solubility in organic solvents. For example, almost polyamide resins dissolved in only special high boiling-point polar solvents having a large dissolving power such as N-methyl-2-pyrrodidone. Thus, when such resins were used as coating resins and subjected to low-temperature baking wherein heat treatment such as drying, curing, and the like were carried out below the boiling point of such high boiling-point solvents, since the solvents were retained in the coating film after baking, not only coating film properties of the polyamide resins originally had were not exhibited sufficiently, but also various undesirable influences due to the retained solvent were generated. Therefore, such polyamides were only used for high-temperature baking wherein the high boiling-point solvents were completely vaporized and flown away.

Recently, in order to solve such a problem, there have been developed and commercially available copolymer-based aliphatic polyamides soluble in lower alcohols having low boiling points, and aliphatic polyamides wherein whole or a part of hydrogen atoms in amide bonds are substituted with alkoxymethyl groups, ethylol groups, etc. Since these polyamides have active amino groups and imino groups in the molecule, they are well used as a curing agent for epoxy resins for coating due to being able to impart properties such as heat resistance, moisture resistance and flexibility inherent to polyamides to epoxy resin cured articles. But since the amino group and imino group are highly reactive with the epoxy group and easily proceed a curing reaction even at room temperature, the pot life (a usable period) is very short even if used as a two-pack type coating composition. Even if the amino group and imino group are neutralized with various acids to form salts which have latent curing properties, it is impossible to obtain a sufficient pot life.

On the other hand, polyamide resins, polyurethane resins and polyurea resins having amide groups in the molecules have a large agglomerating energy due to high polarity of the amide group and the strong hydrogen bond. Particularly the polyamide resins have widely been used as a curing agent or an additive for epoxy resins, since they can provide higher adhesiveness to epoxy resin cured articles due to the large agglomerating energy. But generally speaking, compatibility of polyamide resins with epoxy resins is poor, so that uniform cured articles are not always obtained when the two resins are mixed, and qualities such as adhesive reliability are not always sufficient.

SUMMARY OF THE INVENTION

It is an object of the present invention to provide an amide group-containing diisocyanate compound overcoming disadvantages of prior art and a process for producing the same.

It is another object of the present invention to provide an amide group-containing epoxy resin which can give a uniform cured article having high adhesiveness compared with known epoxy resins, and a process for producing the same.

It is a further object of the present invention to provide an amide group-containing epoxy resin (or polyamide-epoxy resin) which is soluble in general propose solvents having low boiling points, has an excellent pot life providing no problem in practical use, and be usable as a one-pack type coating composition or the like, and a process for producing the same.

The present invention provides an amide group-containing diisocyanate compound of the formula:

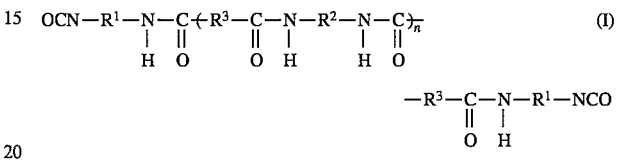

(I)

wherein $R^1$, $R^2$ and $R^3$ are independently a divalent organic group, a plurality of $R^1$'s may be the same or different, and when a plurality of $R^2$'s and $R^3$'s are present, these may be the same or different, respectively; and n is zero or an integer of 1 or more, and a process for producing the same.

The present invention further provides an amide group-containing diisocyanate compound of the formula:

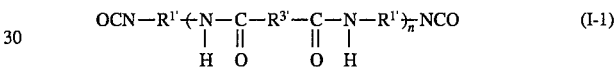

(I-1)

wherein $R^{1'}$ and $R^{3'}$ are independently a divalent organic group, and when a plurality of $R^{1'}$'s and $R^{3'}$'s are present, these may be the same or different, respectively; and n is an integer of 1 or more, and a process for producing the same.

The present invention also provides an amide group-containing epoxy resin obtained from the amide group-containing diisocyanate compound of the formula (I) or (I-1), and a process for producing the same.

DESCRIPTION OF THE PREFERRED EMBODIMENTS

Figure 1:
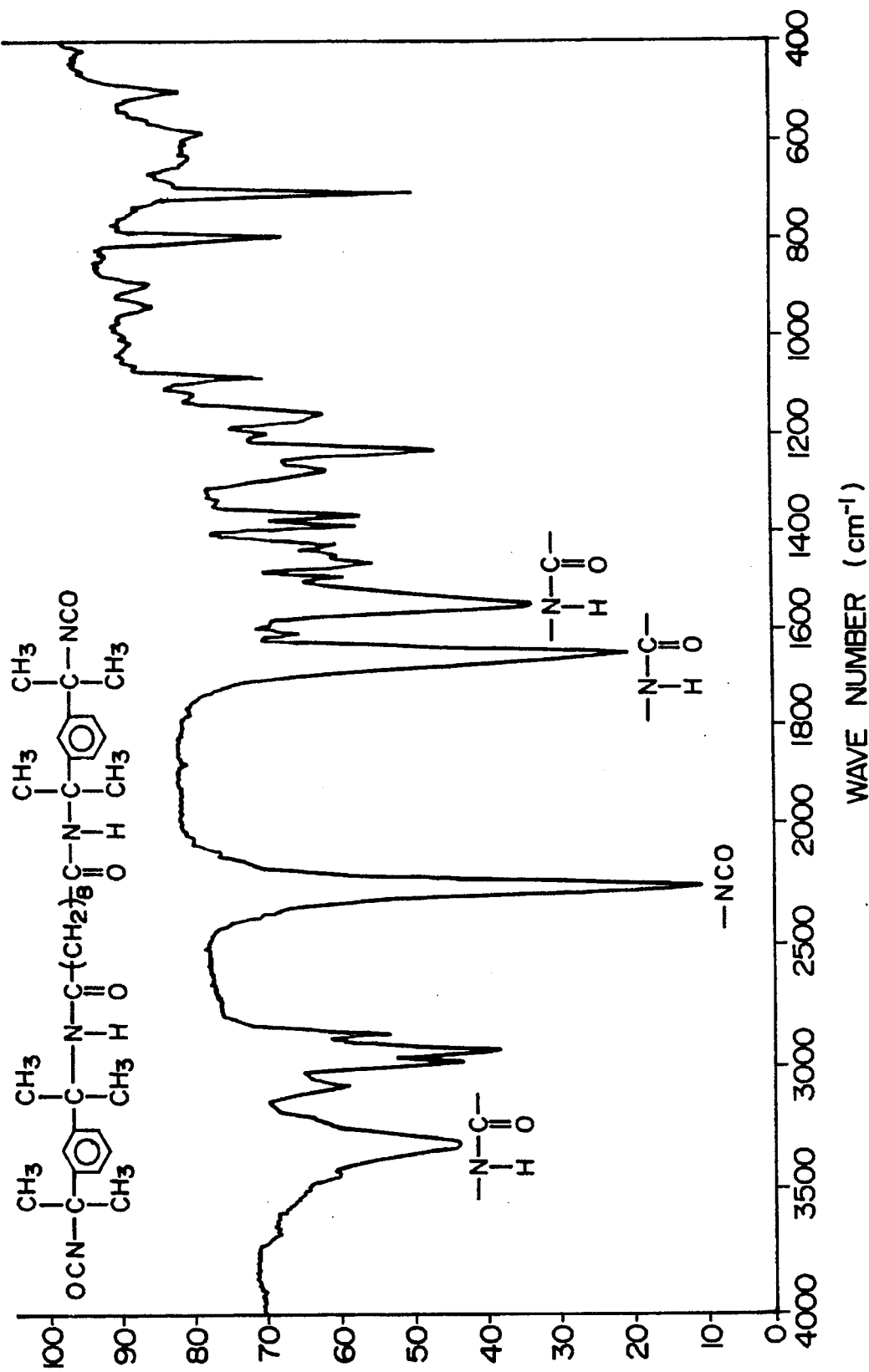
FIG. 1 is an infrared (IR) spectrum of the amide group-containing diisocyanate obtained in Example 1.

The amide group-containing diisocyanate compound of the present invention is represented by the formula:

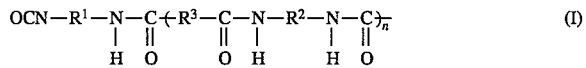

(I)

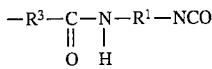

wherein $R^1$ $R^2$ and $R^3$ are independently a divalent organic group such as a straight-chain or branched alkylene group preferably having 1 to 18 carbon atoms, a cycloalkylene group preferably having 3 to 8 carbon atoms, an arylene group preferably having 5 to 18 carbon atoms, an aralkylene group preferably having 6 to 19 carbon atoms, said alkylene group being able to be substituted with one or more alkoxy groups having 1 to 4 carbon atoms or halogen atoms, and said cycloalkylene group, said arylene group and said aralkylene group being able to be substituted with one or more alkyl groups having 1 to 4 carbon atoms, alkoxy groups having 1 to 4 carbon atoms, or halogen atoms; $-(CH_2)_m-O-(CH_2)_n-$ wherein m and n are independently an integer of 1 to 4;

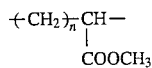

wherein n is an integer of 1 to 4; $-(CH_2)_m-S-(CH_2)_n-$ wherein m and n are independently an integer of 1 to 4;

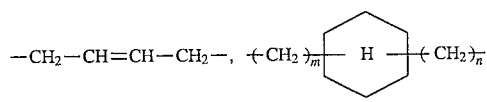

wherein m and n are independently an integer of 1 to 4;

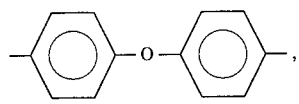

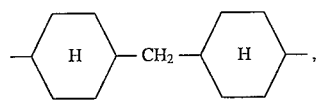

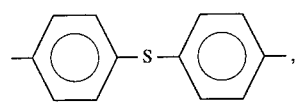

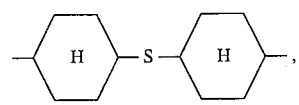

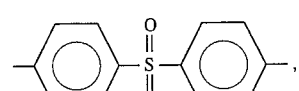

etc.;

and $R^3$ can be a group of the formula;

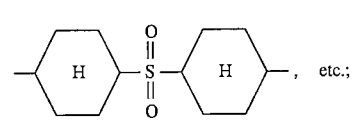

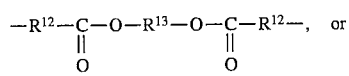

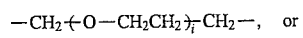

a residue to give the formula;

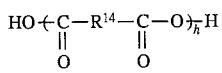

wherein $R^{12}$, $R^{13}$, $R^{14}$, i and h are as defined below, a plurality of $R^1$'s may be the same or different, and when a plurality of $R^2$'s and $R^3$'s are present, these may be the same or different, respectively; and n is zero or an integer of 1 or more.

Further $R^1$ can be represented by the formula:

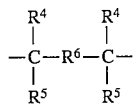 (II)

wherein $R^4$ is a hydrogen atom or a monovalent organic group such as an alkyl group preferably having 1 to 6 carbon atoms, and two $R^4$'s may be the same or different; $R^5$ is a monovalent organic group such as an alkyl group preferably having 1 to 6 carbon atoms, and two $R^5$'s may be the same or different; and $R^6$ is a divalent organic group such as a phenylene group, a naphthylene group, or represented by the formula:

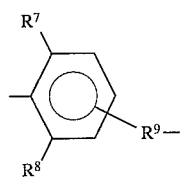 (III)

wherein $R^7$ is a hydrogen atom, a halogen atom such as F, Cl, Br, or I, or a monovalent organic group such as an alkyl group preferably having 1 to 6 carbon atoms, an alkoxy group preferably having 1 to 6 carbon atoms; $R^8$ is a halogen atom such as F, Cl, Br or I, or a monovalent organic group such as an alkyl group preferably having 1 to 6 carbon atoms, an alkoxy group preferably having 1 to 6 carbon atoms, an aralkyl group preferably having 6 to 19 carbon atoms; and $R^9$ is a single bond or a divalent organic group such as a benzylene group, a biphenylene group, etc.; said phenylene group, said benzylene group and said biphenylene group being able to be substituted with one or more alkyl groups having 1 to 4 carbon atoms, alkoxy groups having 1 to 4 carbon atoms or halogen atoms.

$R^2$ can also take the formula (II) or (III).

When $R^1$ or $R^2$ is represented by the formula (II) or (III), better results can be obtained.

The amide group-containing diisocyanate compound of the formula (I) can be produced by a carbon dioxide removal polymerization reaction wherein a diisocyanate of the formula:

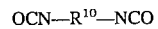 (IV)

wherein $R^{10}$ is the same as $R^1$ or $R^2$, is reacted with a dicarboxylic acid of the formula:

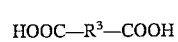 (V)

wherein $R^3$ is as defined above, in a molar ratio of diisocyanate/dicarboxylic acid of more than 1.

Further, the amide group-containing epoxy resin of the present invention is represented by the following formula (VI):

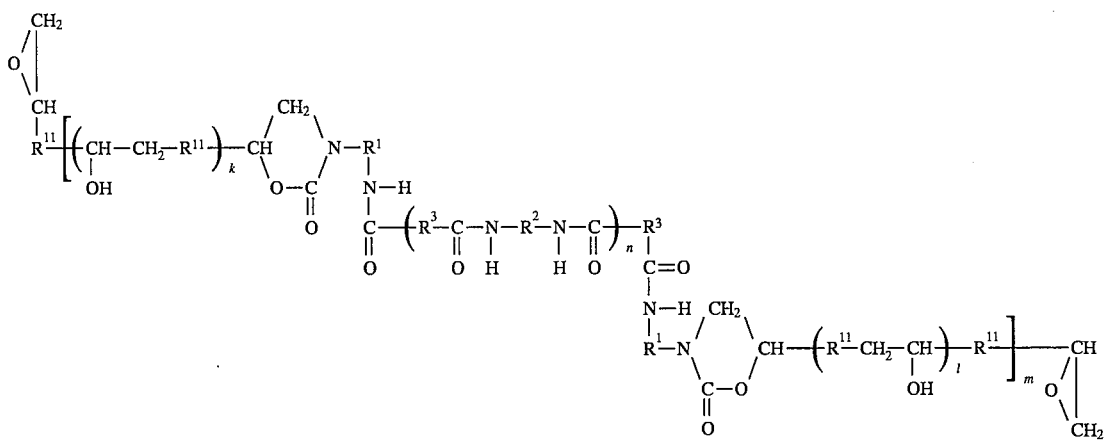

wherein $R^{11}$ is a divalent organic group such as a straight-chain or branched alkylene group preferably having 1 to 18 carbon atoms, a cycloalkylene group preferably having 3 to 8 carbon atoms, an arylene group preferably having 5 to 18 carbon atoms, aralkylene group preferably having 6 to 19 carbon atoms, said alkylene group being able to be substituted with one or more alkoxy groups having 1 to 4 carbon atoms or halogen atoms, and said cycloalkylene group, said arylene group and said aralkylene group being able to be substituted with one or more alkyl groups having 1 to 4 carbon atoms, alkoxy groups having 1 to 4 carbon atoms, or halogen atoms; and a plurality of $R^{11}$'s may be the same or different; $R^1$, $R^2$, $R^3$ and n are as defined above; k is zero or an integer of 1 or more; l is zero or an integer of 1 or more; and m is an integer of 1 or more.

The amide group-containing epoxy resin of the formula (VI) can be produced by reacting the amide group-containing diisocyanate compound of the formula (I) with an epoxy resin of the formula:

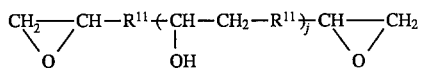

wherein $R^{11}$ is as defined above; and j is the same as k or l, in a molar ratio of epoxy resin/amide group-containing diisocyanate of more than 1.

Examples of the diisocyanate compound of the formula (IV) are as follows: 4,4'-diphenylmethane diisocyanate, 1,5-naphthalene diisocyanate, p-phenylene diisocyanate, hexamethylene diisocyanate, 2,2,4-trimethylhexamethylene diisocyanate, 2,4,4-trimethylhexamethylene diisocyanate, isophorone diisocyanate, 4,4'-dicyclohexylmethane diisocyanate, trans-cyclohexane-1,4-diisocyanate, tolysine diisocyanate, m-xylene diisocyanate, hydrogenated m-xylene diisocyanate, etc.

As the diisocyanate compound, it is possible to use those of the formula:

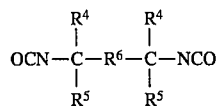

wherein $R^4$, $R^5$ and $R^6$ are as defined above.

Examples of the diisocyanate of the formula (VIII) are as follows:

1,4-bis(1-isocyanato-1-methylethyl)benzene,
1,3-bis(1-isocyanato-1-methylethyl)benzene,
1,4-bis(1-isocyanatoethyl)benzene,
1,3-bis(1-isocyanatoethyl)benzene,
1-(1-isocyanato-1-methylethyl)-4-(1-isocyanatoethyl)benzene,
1-(1-isocyanato-1-methylethyl)-3-(1-isocyanatoethyl)benzene,
1,4-bis(1-isocyanato-1-methylpropyl)benzene,
1,4-bis(1-isocyanato-3-chloropropyl)benzene,
2,5-bis(1-isocyanato-1-methylethyl)naphthalene,
2,5-bis(1-isocyanatoethyl)naphthalene, etc.

As the diisocyanate, it is possible to use those of the formula:

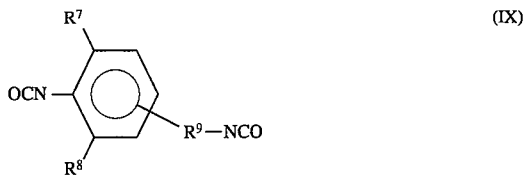

wherein $R^7$, $R^8$ and $R^9$ are as defined above.

Examples of the diisocyanate of the formula (IX) are as follows:

2,4-tolylene diisocyanate,
2,6-tolylene diisocyanate,
3,3'-dimethyldiphenylmethane-4,4'-diisocyanate,
3,3'-dichlorodiphenylmethane-4,4'-diisocynate,
3,3'-bitolylene-4,4'-diisocyanate,
3,3'-dimethylbiphenyl-4,4'-diisocyanate,
3,3'-dimethoxybiphenyl-4,4'-diisocyanate,
2,5,2',5'-tetramethyldiphenylmethane-4,4'-diisocyanate,
3,3'-dimethoxydiphenylmethane-4,4'-diisocyanate,
4,4'-dimethoxydiphenylmethane-3,3'-diisocyanate,
4,4'-diethoxydiphenylmethane-3,3'-diisocyanate,
2,2'-dimethyl-5,5'-dimethoxydiphenylmethane-4,4'-diisocyanate,
3,3'-dichlorodiphenyldimethylmethane-4,4'-diisocyanate, etc.

The diisocyanates of the formulae (IV), (VIII) and (IX) can be used singly or as a mixture thereof.

Among these diisocyanate compounds, those of the formulae (VIII) and (IX) having a group showing a steric hindrance effect which reduces reactivity near at least one isocyanate group among two isocyanate groups are preferable from the viewpoint of hardly bringing about side reactions such as a reversible intermolecular dimerization reaction between isocyanate groups (uretdione producing reaction) and an irreversible intermolecular trimerization reaction (isocyanurate producing reaction). Particularly preferable diisocyanate compounds are those of the formula (VIII) wherein $R^4$ and $R^5$ are methyl groups (steric hindrance group) and $R^6$ is a phenylene group, i.e., 1,4-bis(1-isocyanato-1-methylethyl)benzene and 1,3-bis(1-isocyanato-1-methylethyl)benzene. By using such a diisocyanate having a steric hindrance group, high stability of the isocyanate group in the amide group-containing diisocyanate compound of the formula (I) during and after production thereof can be maintained.

As the dicarboxylic acid of the formula (V), there can be used aromatic dicarboxylic acids such as isophthalic acid, terephthalic acid, phthalic acid, naphthalene dicarboxylic acid, etc.; aliphatic dicarboxylic acids preferably having 4 or more methylene groups therein such as succinic acid, glutaric acid, adipic acid, azelaic acid, sebacic acid, dodecanedioic acid, etc.; alicyclic dicarboxylic acids such as 1,4-dicarboxycyclohexane, dimer acid, etc.

It is also possible to use dicarboxylic acids having two ester bonds and represented by the formula:

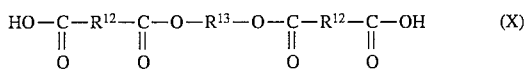

(X)

wherein $R^{12}$ is a residue of cyclic dicarboxylic anhydride, and two $R^{12}$'s may be the same or different; and $R^{13}$ is a residue of diol, obtained by half esterification of 2 moles of cyclic dicarboxylic anhydride such as succinic anhydride with 1 mole of a diol.

Examples of the diol are ethylene glycol, diethylene glycol, triethylene glycol, propylene glycol, dipropylene glycol, 1,6-hexanediol, 1,4-butanediol, 1,3-propanediol, 1,8-octanediol, neopentyl glycol, 1,4-cyclohexane diol, etc.

It is further possible to use dicarboxylic acids represented by the formula:

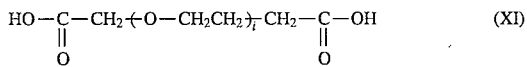

(XI)

wherein i is an integer of 1 or more, preferably 1 to 100, more preferably 1 to 60, most preferably 5 to 20, and those represented by the formula:

(XII)

wherein $R^{14}$ is a divalent organic group; and h is an integer of 1 or more, preferably 1 to 50, more preferably 1 to 30, most preferably 1 to 10.

These dicarboxylic acids of the formulae (V) including (X), (XI) and (XII) can be used singly or as a mixture thereof.

The diisocyanate (A) of the formula (IV) and the dicarboxylic acid (B) of the formula (V) are reacted in a molar ration of (A)/(B) of more than 1, finally. But, it is not necessary to react (A) with (B) in a molar ratio of larger than 1 from the beginning. For example, in an initial stage, (A) can be reacted with (B) in a molar ratio of 1 or less to obtain the desired amide group-containing dicarboxylic acid intermediate, followed by reaction with an insufficient amount of (A). When the final molar ratio of (A)/(B) is 1 or less, the obtained compound has a carboxyl group at one end group or two carboxyl groups at both end groups. The final molar ratio (A)/(B) of 2 or less is preferable. When the final molar ratio is more than 2, (A) is easily retained as an unreacted material.

The amide group-containing diisocyanate compound of the formula (I) can also be produced by reacting a diisocyanate with a diol or diamine in place of that of dicarboxylic acid. As the diol, there can be used a diol which is used for producing the dicarboxylic acids represented by the formula (X). In this case, the amide group in the amide group-containing diisocyanate compound can be introduced in the form of a urethane bond or urea bond.

The amide group-containing diisocyanate compound (I) can be obtained by reacting a diisocyanate of the formula (IV) with a dicarboxylic acid (V) at preferably 50° to 250° C., more preferably 100° to 200° C. (preferably in a substantially anhydrous state) while removing $CO_2$ produced from the reaction system. If necessary, a catalyst can be used in the reaction. As the catalyst, it is convenient to use those having also catalytic activity in the reaction of an epoxy resin of the formula (VII) with the amide group-containing diisocyanate compound (I) to produce an amide group-containing epoxy resin of the formula (VI).

Examples of the catalyst are metallic salts of organic acids such as dibutyltin dilaurate, 1,3-diacetoxy tetrabutyldistannoxane, sodium benzoate, potassium benzoate, etc.; inorganic salts such as zinc chloride, iron chloride, lithium chloride, lithium bromide, etc.; metal carbonyls such as octacarbonyl dicobalt (cobalt carbonyl), etc.; phosphorus compounds such as 3-methyl-1-phenyl-2-phosphorene-1-oxide, etc.; tertiary amines such as triethylamine, triethylenediamine, N,N-dimethylaniline, N,N-diethylaniline, N,N-dimethylbenzylamine, N-methylmorpholine, N-ethylmorpholine, N,N-dimethylpiperazine, pyridine, picoline, 1,8-diazabicyclo[5,4,0]undec-7-ene, etc.; quaternary ammonium salts such as tetraethylammonium bromide, tetrabutylammonium bromide, benzyltriethylammonium chloride, trioctylmethylammonium chloride, cetyltrimethylammonium bromide, tetrabutylammonium iodide, dodecyltrimethylammonium iodide, benzyldimethyltetradecylammoniumacetate, etc.; quaternary phosphonium salts such as tetraphenyl phosphonium chloride, triphenylmethyl phosphonium chloride, tetramethyl phosphonium bromide, etc.; imidazole compounds such as 2-methylimidazole, 2-ethylimidazole, 2-ethyl-4-methylimidazole, 2-methyl-4-methylimidazole, 1-cyanoethyl-2-methylimidazole, 1-cyanoethyl-2-phenylimidazole, 2-phenyl-4-methyl-5-hydroxymethylimidazole, 2-phenyl-4,5-dihydroxymethylimidazole, 1-azine-2-methylimidazole, etc. These compounds can be used singly or as a mixture thereof.

If necessary, a solvent can be used. Examples of the solvent are N-methyl-2-pyrrolidone, N,N-dimethylacetamide, N,N-dimethylformamide, N,N'-dimethylethyleneurea, N,N-dimethylpropyleneurea, tetramethylurea, γ-butyrolactone, sulfolane, diethylene glycol dimethyl ether, ethyl acetate, n-butyl acetate, methyl ethyl ketone, methyl isobutyl ketone, etc. These solvents can be used singly or as a mixture thereof.

The epoxy resin represented by the formula (VII) has two or more epoxy groups in the molecule, and can be saturated aliphatic or unsaturated aliphatic epoxy resins, alicyclic epoxy resins, aromatic epoxy resins and heterocyclic epoxy resins. Further, the epoxy resin can have one or more substituents such as epoxy groups, hydroxyl group, halogen atoms, etc.

Examples of the epoxy resin of the formula (VII) are as follows:

Aromatic glycidyl ether compounds:
  bisphenol A type, e.g. 4,4'-isopropylidene bisphenol diglycidyl ether,
  bisphenol F type, e.g. 4,4'-methylene bisphenol diglycidyl ether,
  brominated bisphenol A type, e.g. 2,6,2',6'-tetrabromo-4,4'-isopropylidene bisphenol diglycidyl ether,
  phenol novolak type polyglycidyl ethers, ortho-cresol novolak type polyglycidyl ethers, etc.
Aliphatic glycidyl ether compounds:
  ethylene glycol diglycidyl ether,
  polyethylene glycol diglycidyl ether,
  propylene glycol diglycidyl ether,
  polypropylene glycol diglycidyl ether,
  neopentyl glycol diglycidyl ether,
  1,6-hexanediol diglycidyl ether,
  glycerol diglycidyl ether, glycerol triglycidyl ether,
  trimethylolpropane diglycidyl ether, trimethylolpropane triglycidyl ether,
  hydrogenolyzed bisphenol A type diglycidyl ethers,
  sorbitol polyglycidyl ether,
  2,2'-dibromo-neopentyl glycol diglycidyl ether, etc.
Glycidyl ester compounds:
  phthalic-acid diglycidyl ester,
  tetrahydrophthalic acid diglycidyl ester,
  hexahydrophthalic acid diglycidyl ester, etc.
Glycidyl amine compounds:
  N,N-diglycidyl aniline,
  N,N,N',N'-tetraglycidyl-4,4'-diaminodiphenylmethane,
  1,3-bis(N,N-diglycidylaminomethyl)cyclohexane,
  N,N,O-triglycidyl-p-aminophenol, etc.
Alicyclic epoxy compounds;
  alicyclic diepoxy acetal,
  alicyclic diepoxy adipate,
  alicyclic diepoxy carboxylate,
  vinyl cyclohexene dioxide, etc.
Heterocyclic epoxy compounds;
  diglycidyl hydantoin,
  triglycidyl isocyanurate, etc.

Among these epoxy resins, bisphenol A type epoxy resins are preferable, and brominated bisphenol A type epoxy resins are particularly preferable from the viewpoint of imparting flame retardancy. These epoxy resins can be used singly or as a mixture thereof.

The amide group-containing epoxy resin of the formula (VI) can be produced by reacting an epoxy resin (C) represented by the formula (VII) with an amide group-containing diisocyanate compound (D) represented by the formula (I) in a molar ratio of (C)/(D) of more than 1. When the molar ratio of (C)/(D) is more than 2,2, the epoxy resin is to be retained as an unreacted material. When no catalyst is used, the molar ratio of (C)/(D) is preferably more than 1 and 2,2 or less, while when a catalyst is used, the molar ratio of (C)/(D) is preferably 2 to 2,2. In such a case, a large excess of epoxy resin is used to produce the desired amide group-containing epoxy resin, followed by purification.

The purification method is not particularly limited. For example, the reaction product is washed with a suitable solvent which dissolves only the unreacted epoxy resin, followed by removal of the unreacted epoxy resin. As such a solvent, for example xylene can be used.

The reaction of the amide group-containing diisocyanate compound of the formula (I) with the epoxy resin of the formula (VII) can be carried out at a temperature of 80° C. or higher, preferably 120° to 180° C., more preferably 140° to 160° C. (preferably in a substantially anhydrous state). When the reaction temperature is lower than 80° C., the isocyanate group of the amide group-containing diisocyanate compound of the formula(I) reacts with the secondary hydroxyl group of the epoxy resin of the formula (VII) to produce a byproduct having urethane bonds formed by addition reaction. On the other hand, when the reaction temperature is higher than 180° C., there easily take place side reactions wherein functional groups such as isocyanate groups, epoxy groups, amide groups, secondary hydroxyl groups, etc. pertain complicatedly mutually, and sometimes gelation takes place during the reaction.

The addition reaction between an isocyanate group and an epoxy group which is an elementary reaction for producing the amide group-containing epoxy resin of the formula (VI), can proceed gradually even in the absence of a catalyst since an amide group functions as a catalyst. In order to enhance the reaction rate with high reactivity, it is possible to use a catalyst. As the catalyst, there can be used those used for the carbon dioxide removal polymerization reaction for producing the amide group-containing diisocyanate compound of the formula (I). Such catalysts can be used as a mixture thereof.

If necessary, a solvent can be used for the reaction. As the solvent, those used for the carbon dioxide removal polymerization reaction for producing the amide group-containing diisocyanate compound of the formula (I) singly or as a mixture thereof.

The amide group-containing epoxy resin of the formula (VI) can be mixed with, if necessary, one or more conventional curing agents for epoxy resins, conventional curing accelerators for epoxy resins, epoxy resins of the formula (VII), monoepoxy compounds, and various additives, depending on purposes. Further, it can be modified with various reactive compounds having amino groups, imino groups, carboxyl groups, or the like in the molecule. Thus, it can be used as an adhesive, a coating composition, a molding material for producing electric and electronic parts and the like.

Further, the amide group-containing diisocyanate compound of the formula (I) can be-used not only for producing the amide group-containing epoxy resin of the formula (VI) but also as a starting material for producing other resins, as a curing agent for various thermosetting resins in the form of a blocked isocyanate derivative obtained by adding a blocking agent such as an alcohol for blocking an isocyanate group.

In the present invention, an amide group-containing diisocyanate compound of the formula:

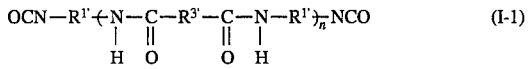

(I-1)

wherein $R^{1'}$ and $R^{3'}$ are independently a divalent organic group as defined in the formula (I) for $R^1$ and $R^3$, and when a plurality of $R^{1'}$s and $R^{3'}$s are present, these may be the same or different; and n is an integer of 1 or more, is also effective.

When $R^{1'}$ is represented by the formula:

(II-1)

and n is an integer of 1 in the formula (I-1), the resulting compound is preferable.

The amide group-containing diisocyanate compound of the formula (I-1) can be produced by reacting a diisocyanate compound of the formula:

(IV-1)

wherein $R^{1'}$ is as defined above, with a dicarboxylic acid of the formula;

(V-1)

wherein $R^{3'}$ is as defined above, in a molar ratio of diisocyanate/dicarboxylic acid of more than 1.

Further, an amide group-containing epoxy resin (or polyamide-epoxy resin) of the formula:

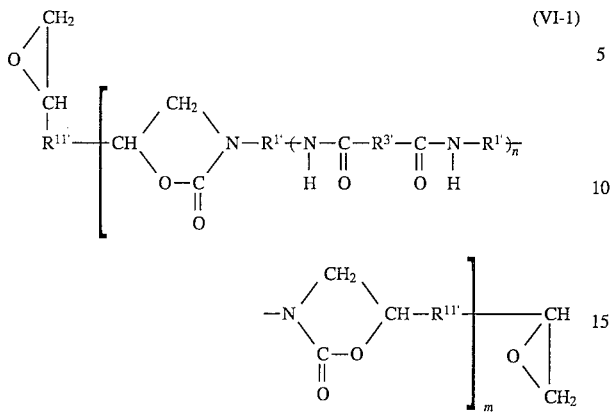

wherein $R^{11'}$ is a divalent organic group, and a plurality of $R^{11'}$s may be the same or different; $R^{1'}$, $R^{3'}$ and n are as defined above; and m is an integer of 1 or more, is also effective.

The polyamide-epoxy resin of the formula (VI-1) can be produced by reacting the amide group-containing diisocyanate compound of the formula (I-1) with an epoxy compound of the formula:

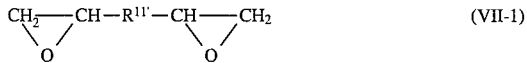

wherein $R^{11'}$ is as defined above, in a molar ratio of epoxy compound/amide group-containing diisocyanate comound of more than 1.

Examples of the diisocyanate compound of the formula (IV-1) are as follows:
diphenylmethane diisocyanate,
a hydrogenated product thereof,
xylene diisocyanate,
a hydrogenated products thereof,
tolylene diisocyanate,
1,5-naphthalene diisocyanate,
tolidine diisocyanate,
p-phenylene diisocyanate,
hexamethylene diisocyanate,
trimethylhexamethylene diisocyanate,
isophorone diisocyanate,
trans-cyclohexane-1,4-diisocyanate, etc.

As the diisocyanate compound, it is possible to use tetramethylxylene diisocyanate of the formula:

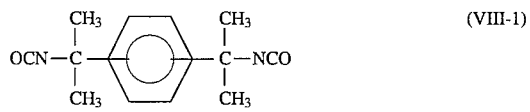

These diisocyanate compounds can be used singly or as a mixture thereof.

Among these diisocyanate compounds, tetramethylxylene diisocyanate of the formula (VIII-1) is preferable, since when the diisocyanate having a bulky alkyl group at the carbon atom adjacent to the isocyanate group, the resulting polyamide-epoxy resin has remarkably excellent solubility in an organic solvent due to suppression of the intermolecular hydrogen bond in the amide bond by the steric hindrance of the above-mentioned alkyl group. Tetramethylxylene diisocyanate can preferably be mixed with other diisocyanate compounds of the formula (IV-1) in a proportion of 50% by mole of the former and less than 50% by mole of the latter, so long as the solubility of the resulting polyamide-epoxy resin of the formula (VI-1) is not damaged.

As the dicarboxylic acid of the formula (V-1), there can be used aliphatic dicarboxylic acids which can provide high solubility to the resulting polyamide-epoxy resin of the formula (VI-1). Examples of the aliphatic dicarboxylic acids are adipic acid, azelaic acid, sebacic acid, dodecanedioic acid, etc., wherein a main chain is constituted by a methylene chain, preferably having 4 or more methylene groups.

It is also possible to use a half ester of the formula:

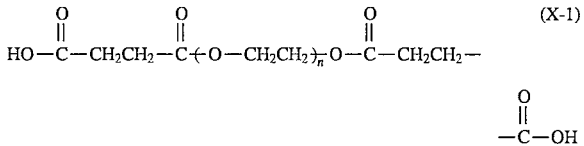

wherein n is an integer of 1 to 100, obtained by addition reaction of alicyclic dicarboxylic anhydride such as succinic anhydride to both terminal hydroxyl groups of ethylene glycol, polyethylene glycol such as diethylene glycol, triethylene glycol, etc.

It is further possible to use a poly(oxyethylene)diglycolic acid of the formula:

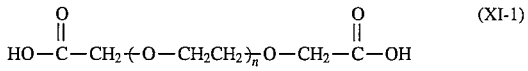

wherein n is an integer of 1 to 100.

Among these dicarboxylic acids, the use of sebacic acid is preferable from the viewpoint of the purity and yield of the diisocyanate compound of the formula (I-1) When sebacic acid is used, $R^{3'}$ in the formula (I-1) becomes an alkylene group having 8 carbon atoms as a residue of sebacic acid.

The diisocyanate compound (A') of the formula (IV-1) and the dicarboxylic acid (B') of the formula (V-1) are reacted in a molar ratio of (A')/(B') of substantially more than 1 to prepare the diisocyanate of the formula (I-1) having isocyanate groups at both terminals. When the molar ratio of (A')/(B') is 1 or less, the resulting polyamide is to have a carboxyl group at one terminal or both terminals. It is preferable to make the molar ratio of (A')/(B') 2 or less. When the molar ratio is more than 2, there is a tendency to retain the diisocyanate compound of the formula (IV-1) as an unreacted material.

The carbon dioxide removal polymerization reaction of the diisocyanate compound (A') of the formula (IV-1) with the dicarboxylic acid (B') of the formula (V-1) to prepare the diisocyanate of the formula (I-1) can be carried out preferably at 80° to 250° C. in the presence of a catalyst, more preferably at 100° to 200° C., in a substantially anhydrous state.

As the catalyst, it is preferable to use catalysts which can also function as catalysts in the following reaction with the epoxy compound of the formula (VII-1).

Examples of the catalysts are metallic salts of organic acids such as sodium benzoate, potassium benzoate, dibutyltin dilaurate, 1,3-diacetoxy tetrabutyldistannoxane, etc.; inorganic salts such as zinc chloride, iron chloride, lithium chloride, etc.; tertiary amines such as triethylamine, triethylenediamine, N,N'-dimethylpiperazine, pyridine, picoline, N,N-dimethylbenzylamine, N-methylmorpholine, etc.; halogen-containing quaternary ammonium salts such as tetraethyl-ammonium bromide, tetrabutylammonium iodide, etc. Among these catalysts, the use of alkali metal salts of organic acids such as sodium benzoate and potassium benzoate, and halogen-containing quaternary ammonium salts such as tetraethylammonium bromide and tetrabutyl-ammonium iodide is preferable. These catalysts can be used singly or as a mixture thereof.

It is preferable to use the catalyst in an amount of 0.1 to 10% by mole per mole of the diisocyanate compound (A') of the formula (IV-1).

As a solvent, it is possible to use those which do not damage the carbon dioxide removal polymerization reaction of the diisocyanate compound (A') of the formula (IV-1) and the dicarboxylic acid (B') of the formula (V-1). But considering the easiness of completion of the reaction, it is preferable to keep the reaction system in a non-solvent state with a uniformly molten state.

As the epoxy compound (C') of the formula (VII-1), the following ones can be used.

Aromatic glycidyl ether compounds:
  4,4'-isopropylidene bisphenol diglycidyl ether (bisphenol A type),
  4,4'-methylene bisphenol diglycidyl ether (bisphenol F type),
  2,6,2',6'-tetrabromo-4,4'-isopropylidene bisphenol diglycidyl ether (brominated bisphenol A type),
  phenol novolak type polyglycidyl ethers,
  ortho-cresol novolak type polyglycidyl ethers, etc.

Aliphatic glycidyl ether compounds:
  ethylene glycol diglycidyl ether,
  polyethylene glycol diglycidyl ether,
  propylene glycol diglycidyl ether,
  polypropylene glycol diglycidyl ether,
  neopentyl glycol diglycidyl ether, 1,6-hexanediol diglycidyl ether,
  glycerol diglycidyl ether,
  glycerol triglycidyl ether,
  trimethylolpropane diglycidyl ether,
  trimethylolpropane triglycidyl ether,
  hydrogenolyzed bisphenol A type diglycidyl ethers,
  sorbitol polyglycidyl ether,
  2,2'-dibromo-neopentyl glycol diglycidyl ether, etc.

Glycidyl ester compounds:
  phthalic acid diglycidyl ester,
  tetrahydrophthalic acid diglycidyl ester,
  hexahydrophthalic acid diglycidyl ester, etc.

Glycidyl amine compounds:
  N,N-diglycidyl aniline,
  N,N,N',N'-tetraglycidyl-4,4'-diaminodiphenylmethane,
  1,3-bis(N,N-diglycidylaminomethyl)cyclohexane,
  N,N,O-triglycidyl-p-aminophenol, etc.

Alicyclic epoxy compounds:
  alicyclic diepoxy acetal,
  alicyclic diepoxy adipate,
  alicyclic diepoxy carboxylate,
  vinyl cyclohexene dioxide, etc.

Heterocyclic epoxy compounds:
  diglycidyl hydantoin,
  triglycidyl isocyanurate, etc.

These epoxy compounds can be used singly or as a mixture thereof.

Among these epoxy compounds, the use of 4,4'-isopropylidene bisphenol diglycidyl ether (bisphenol A type) is preferable from the viewpoint of heat resistance. Further, from the viewpoint of providing high solubility in a low boiling point general purpose solvent to the resulting polyamide-epoxy resin, the use of aliphatic glycidyl ether compounds, particularly diglycidyl ethers of glycols, is preferable.

The epoxy compound (C') of the formula (VII-1) and the diisocyanate compound (D') of the formula (I-1) obtained by reacting the diisocyanate compound (A') of the formula (IV-1) with the dicarboxylic acid (B') of the formula (V-1), are reacted in a molar ratio of (C')/(D') of more than 1. For example, when an epoxy compound having two epoxy groups in the molecule is used, a terminal isocyanate group of the amide group-containing diisocyanate is addition reacted with an epoxy group of the epoxy compound (C') to form a 2-oxazolidone ring, by which the rest of the epoxy group of the epoxy compound (C') is introduced into a terminal of the amide group-containing diisocyanate as shown in the following equation (XIII). On the other hand, when the molar ratio is more than 2.2, unreacted epoxy compound (C') is retained. Considering this, the molar ratio of (C')/(D') of more than 1 and 2.2 or less is preferable when no catalyst is used, and 2 to 2.2 is preferable when a catalyst is used.

$$\begin{array}{c} -R^{3'}-\underset{\|}{C}-\underset{|}{N}-R^{1'}-N=C=O + CH_2-CH-R^{11'}-CH-CH_2 \\ O\ \ H \qquad\qquad \diagdown O \diagup \qquad \diagdown O \diagup \end{array} \quad (XIII)$$

$$\downarrow$$

$$-R^{3'}-\underset{\|}{C}-\underset{|}{N}-R^{1'}-N\underset{\underset{\|}{C}-O}{\overset{\overset{CH_2}{\diagup\ \diagdown}}{\diagdown\ \diagup}}CH-R^{11'}-CH-CH_2$$

wherein $R^{1'}$, $R^{3'}$, and $R^{11'}$ are as defined above

The reaction for forming 2-oxazolidone ring between a terminal isocyanate group of the diisocyanate compound of the formula (I-1) and an epoxy group of the epoxy compound of the formula (VII-1) can be carried out in the presence of a catalyst and in a substantially anhydrous state, since the reacting between the isocyanate group and the epoxy group is low.

As the catalyst for the 2-oxazolidone ring formation reaction, there can be used those used for the carbon dioxide removal polymerization reaction between the diisocyanate of the formula (IV-1) and the dicarboxylic acid of the formula (V-1) for producing the diisocyanate of the formula (I-1). Among these catalysts, the use of an alkali metal salt of organic acid such as sodium benzoate, potassium benzoate, or the like is preferable from the viewpoint of reaction rate. The catalyst can be used in an amount of 0.1 to 10% by mole per mole the diisocyanate compound of the formula (IV-1). These catalysts can be used singly or as a mixture thereof.

The reaction of the amide group-containing diisocyanate compound of the formula (I-1) with the epoxy compound of the formula (VII-1) can be carried out preferably at 100° to 170° C. When the reaction temperature is higher than 170° C., the amide bond in the diisocyanate compound of the formula (I-1) with an epoxy group often takes place to proceed rapidly self-cure by three-dimensional crosslinking between molecules, resulting in easily bringing about gelation of the system during the reaction. On the other hand, when the reaction temperature is lower than 100° C., it is difficult to complete the 2-oxazolidone ring formation reaction.

As a solvent, it is possible to use those which do not damage the 2-oxazolidone ring formation reaction between a terminal isocyanate group of the diisocyanate compound of the formula (I-1) and an epoxy group of the epoxy compound of the formula (VII-1). But considering the easiness of completion of the reaction, it is preferable to keep the reaction system in a nonsolvent state with a uniformly molten state.

The polyamide-epoxy resin of the formula (VI-1) is most preferably obtained by the synthesis without using a solvent through the whole processes with a uniformly molten state. After introducing epoxy groups into the terminals, the resulting product is dissolved with a suitable general purpose solvent having a low boiling point to give a coating composition.

As the solvent having a low boiling point, there can be used those having a boiling point of 150° C. or lower and being able to dissolve the polyamide-epoxy resin of the formula (VI-1). Examples of the solvent are lower alcohols such as n-propanol, isopropanol, n-butanol, etc.; aliphatic esters such as ethyl acetate, n-butyl acetate, etc.; aliphatic ketone such as methyl ethyl ketone, methyl isobutyl ketone, etc.; aromatic hydrocarbons such as toluene, xylene, etc. These solvents can be used singly or as a mixture thereof.

The polyamide-epoxy resin of the formula (VI-1) thus produced are stable at room temperature and can be self-cured at a temperature higher than 170° C. Details of this curing reaction is explained in the article by Mukoyama et al: Thermosetting Resins, vol. 6, No. 1, p. 1 (1985). The curing reaction seems to proceed by the following equation (XIV), wherein an insertion reaction of an epoxy group takes place between the carbon atom-nitrogen atom in the amide bond, followed by an addition reaction of an epoxy group to an imino group produced by cleavage of the amide bond. As a result, three-dimensional crosslinking takes place among the molecules to accomplish the self-cure. In the equation (XIV), $R^{14}$, $R^{15}$ and $R^{16}$ are organic groups.

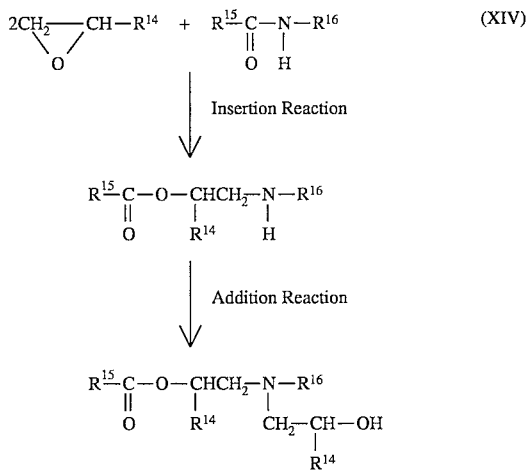

The polyamide-epoxy resin of the formula (VI-1) can be mixed with, if necessary, one or more conventional curing agents for epoxy resins to give two-pack products, one or more epoxy compounds of the formula (VII-1), monoepoxy compounds, various epoxy resin curing accelerators (curing catalysts), and various additives, depending on purposes. Further, it can be modified with various reactive compounds having amino groups, imino groups, etc. in the molecule. Thus, it can be used as an adhesive, a coating composition, and the like.

The present invention is illustrated by way of the following Examples, in which all percents are by weight, unless otherwise specified.

EXAMPLE 1

In a 1-liter separable flask equipped with a stirrer, a thermometer, a cooling condenser, and a nitrogen gas-introducing pipe, 171.1 g (0.700 mole) of m-tetramethylxylene diisocyanate, 70.9 g (0.350 mole) of sebacic acid and 1.01 g (0.007 mole) of sodium benzoate were placed and heated to 130° C. in a nitrogen atmosphere. During the temperature rise, the reaction system became a uniform molten state and generation of $CO_2$ gas was admitted. After the temperature rise, the reaction was carried out at 130° C. for 2 hours and at 170° C. for 3 hours to yield an amide group-containing diisocyanate having isocyanate groups at both terminals.

Figure 2:
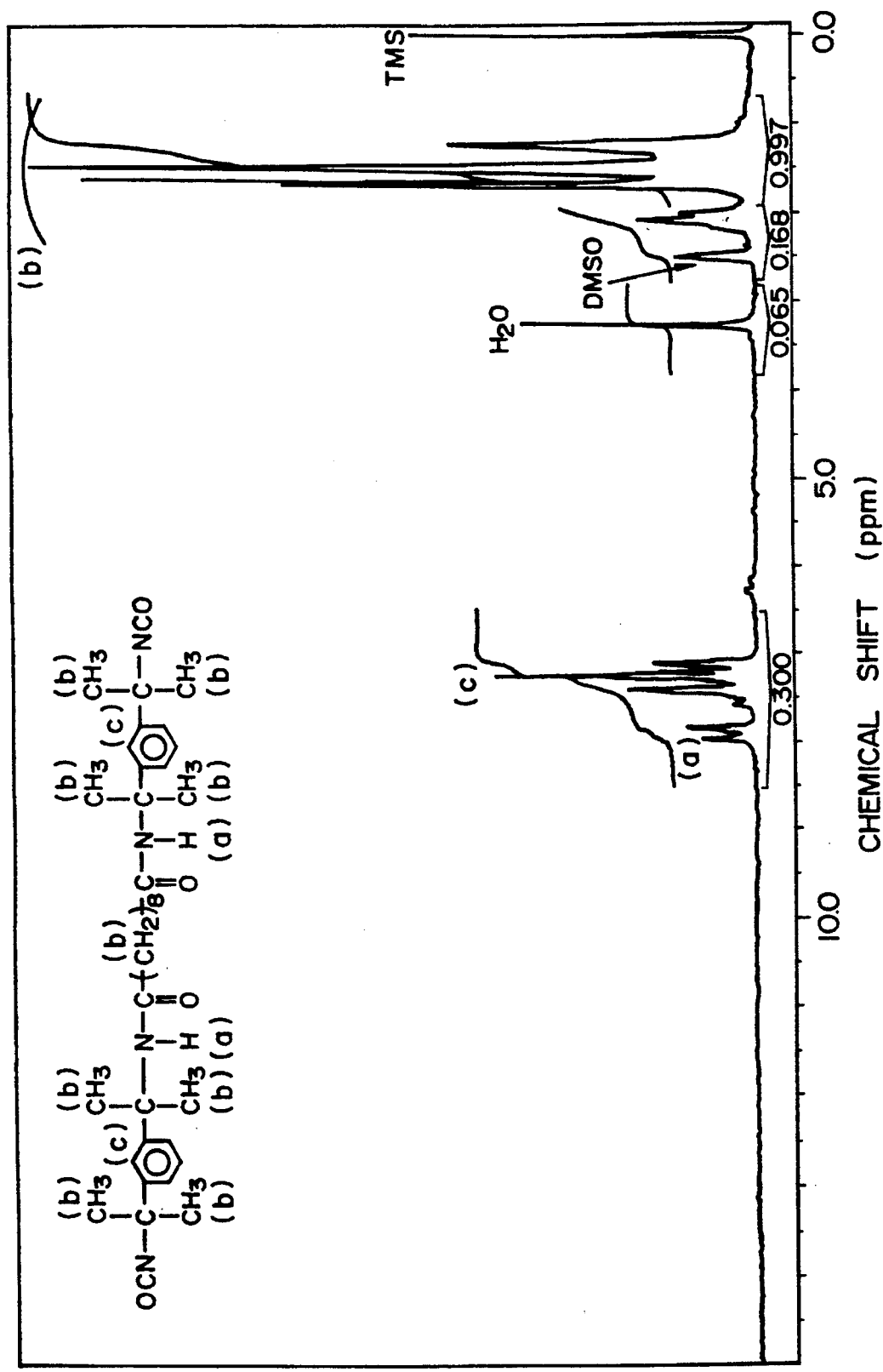
FIG. 2 is a $^1$H-NMR spectrum of the amide group-containing diisocyanate obtained in Example 1.

The amide group-containing diisocyanate was subjected to measurement of infrared (IR) spectrum, which is shown in FIG. 1. In FIG. 1, the absorption of carbonyl group due to the amide bond appears at 1658 $cm^{-1}$, the absorption of imino group due to the amide bond appears at 3320 $cm^{-1}$ and 1548 $cm^{-1}$, and the absorption due to isocyanate group appears at 2260 $cm^{-1}$. $^1$H-NMR spectrum of the amide group-containing diisocyanate is shown in FIG. 2, wherein the integrating intensity ratio is (a)/(c), the theoretical value is 1/4, and the measured value is 1/3.9. In FIG. 2, there are admitted peaks at 7.0–7.6 ppm due to proton of aromatic ring, and at 7.8–8.0 ppm due to proton of imino group in the amide bond. It was admitted that the theoretical values and the measured values of the integrating intensity ratios of these peaks were almost agreed.

Then, to the amide group-containing diisocyanate maintained at 160° C., 157.0 g (0.701 mole) of ethylene glycol diglycidyl ether (Denacol EX-810, a trade name, mfd. by Nagase Chemicals, Ltd.) was dropped in 10 minutes and reacted at 160° C. for 8 hours to yield a polyamide-epoxy resin of the following formula (VI-2).

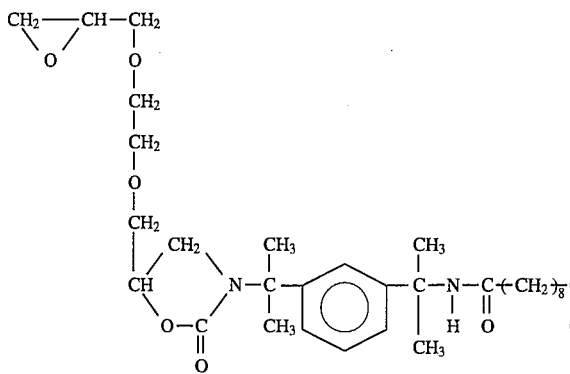

(VI-2)

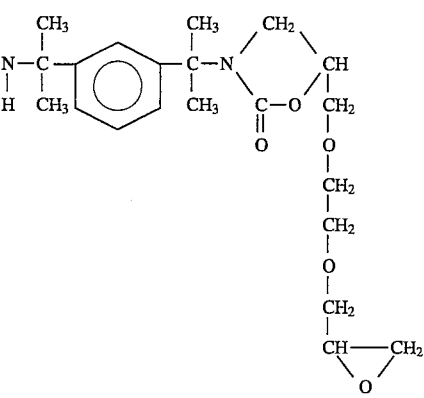

Figure 3:
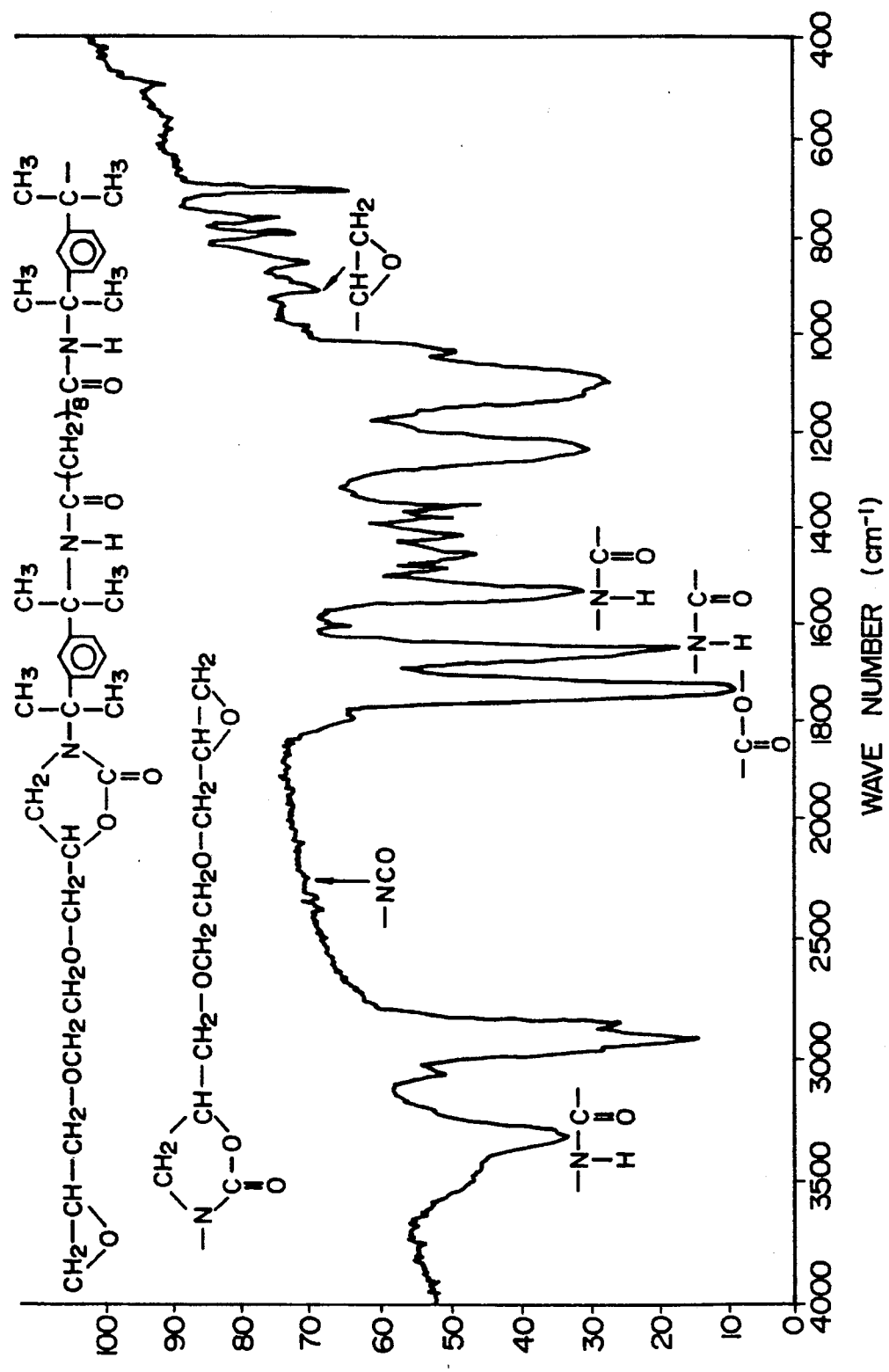
FIG. 3 is an IR spectrum of the amide group-containing epoxy resin obtained in Example 1.
Figure 4:
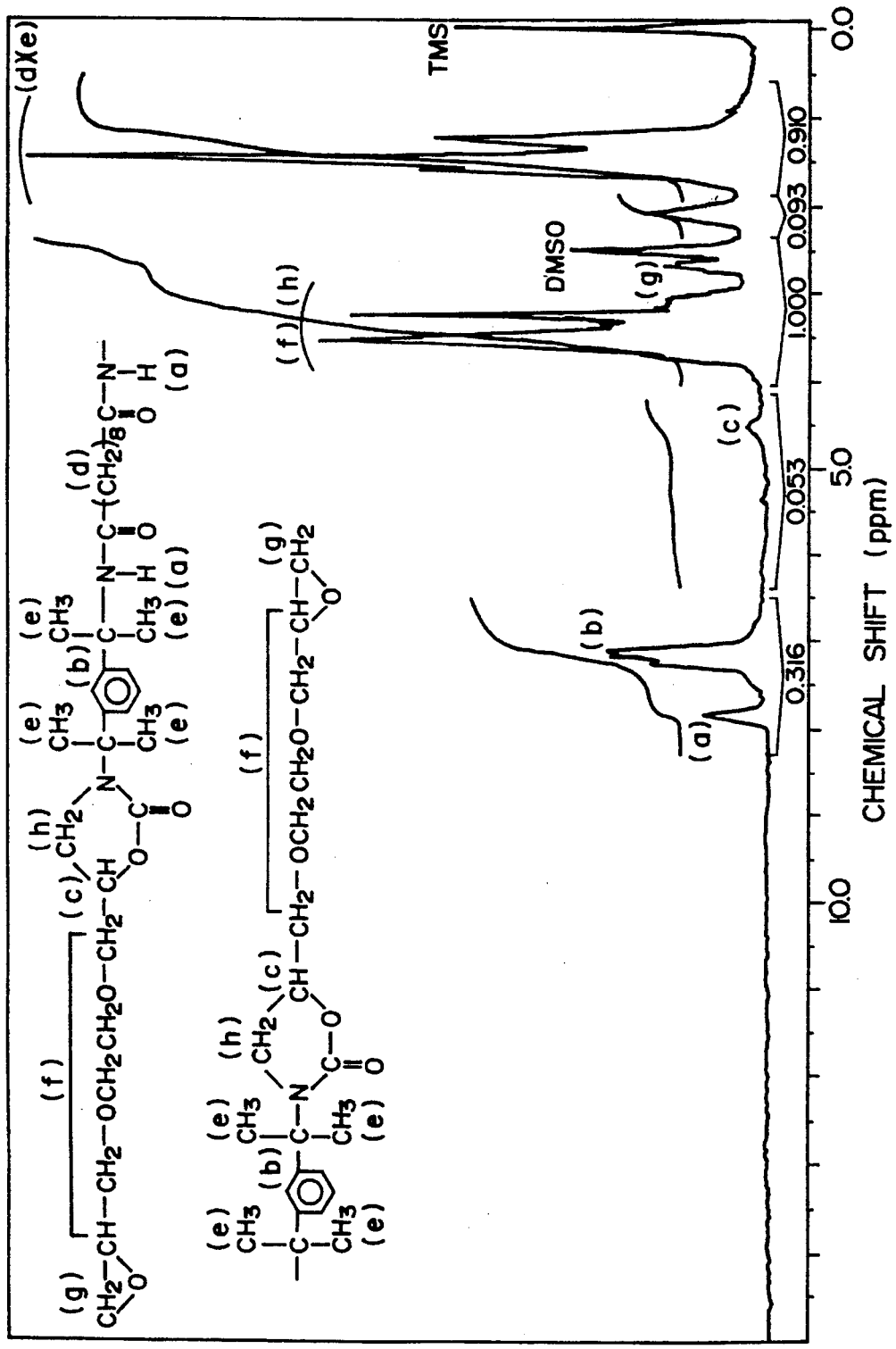
FIG. 4 is a $^1$H-NMR spectrum of the amide group-containing epoxy resin obtained in Example 1.

The polyamide-epoxy resin of the formula (VI-2) was subjected to measurement of IR spectrum, which is shown in FIG. 3. In FIG. 3, there are admitted absorptions at 1658 cm$^{-1}$ due to carbonyl group based on the amide bond, at 3320 cm$^{-1}$ and 1540 cm$^{-1}$ due to imino group based on the amide bond, and at 915 cm$^{-1}$ due to oxirane ring of epoxy group, and also admitted appearance of absorption at 1740 cm$^{-1}$ due to carbonyl group based on the ester bond of 2-oxazolidone ring, and disappearance of absorption at 2260 cm$^{-1}$ due to isocyanate group. $^1$H-NMR of the polyamide-epoxy resin is shown in FIG. 4, wherein the integrating intensity ratio is (a)/(b)/(g), the theoretical value is 1/4/2, and the measured value is 1/4.3/2. In FIG. 4, there are admitted peaks at 7.0–7.6 ppm due to proton of aromatic ring, at 7.8–8.0 ppm due to proton of imino group in the amide bond, and at 2.7 ppm due to methylene group in the oxirane ring of epoxy group. It was admitted that the theoretical values and the measured values of the integrating intensity ratios of these peaks were almost agreed.

Further, it was admitted that the polyamideepoxy resin of the formula (VI-2) was able to be dissolved in n-butanol in 30% or more and showed excellent solubility in general-purpose solvents having low boiling points. The 40% n-butanol solution of the polyamide-epoxy resin of the formula (VI-2) was stable at room temperature for 6 months or more without a large viscosity change and admitted to have an excellent pot life without any problems in practical use.

When the polyamide-epoxy resin of the formula (VI-2) was heat treated at 180° C. for 1 hour, it became insoluble in various organic solvents including N-methyl-2-pyrrolidone which is a polar solvent having great solubility, and was admitted to be self-cured due to three-dimensional crosslinking among molecules. The IR spectrum of this cured article showed disappearance of absorption of oxirane ring due to epoxy group at 915 cm$^{-1}$, and appearance of broad absorption at near 3400 cm$^{-1}$ due to the secondary hydroxyl group produced by addition reaction of epoxy group to the imino group produced by cleavage of amide bond as shown in the equation (XIV).

EXAMPLE 2

In the same reactor as used in Example 1, 11.4 g (0.184 mole) of ethylene glycol, 19.5 g (0.184 mole) of diethylene glycol, 73.6 g (0.736 mole) of succinic anhydride and 1.06 g (0.007 mole) of sodium benzoate were placed in a nitrogen atmosphere and heated to 100° C. During the temperature rise, the reaction system became a uniformly molten state. After the temperature rise, the reaction was carried out at 100° C. for 2 hours to give a liquid mixture containing a dicarboxylic acid of the following formula (X-1) wherein n is 1 in an amount of 50% by mole and a dicarboxylic acid of the following formula (X-1) wherein n is 2 in an amount of 50% by mole:

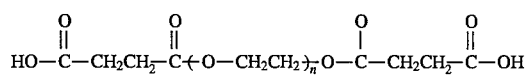

(X-1)

IR spectrum of this dicarboxylic acid mixture showed appearance of broad absorptions at 1740 cm$^{-1}$ due to carbonyl group based on ester bond of terminal carboxyl group, and carbonyl group based on ester bond placed via two methylene chains, and disappearance of absorption at 1785 cm$^{-1}$ and 1870 cm$^{-1}$ due to carbonyl group based on acid anhydride group of succinic anhydride.

Then, this dicarboxylic acid was cooled to room temperature, followed by addition of 179.7 g (0.736 mole) of m-tetramethylxylene diisocyanate to yield an amide group-containing diisocyanate having isocyanate groups at both terminals in the same manner as described in Example 1. Then, the resulting amide group-containing diisocyanate was maintained at 160° C., followed by dropping of 164.9 g (0.736 mole) of ethylene glycol diglycidyl ether (Denacol EX-810, a trade name, mfd. by Nagase Chemicals, Ltd.) in 10 minutes. After reacting at 160° C. for 3 hours, there was obtained a polyamide-epoxy resin of the formula (VI-3) wherein n=1 is present in 50% by mole and n=2 is present in 50% by mole.

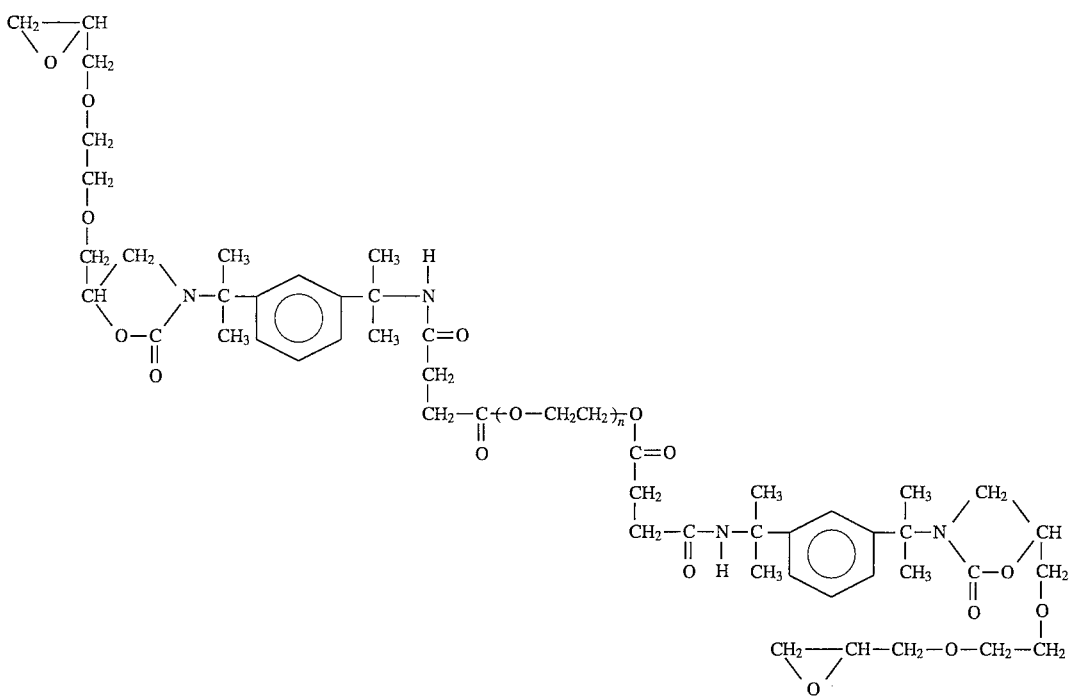

When IR spectrum of this polyamide-epoxy resin was measured, absorption of carbonyl group due to the amide bond and ester bond of 2-oxazolidone ring, absorption of imino group due to the amide bond and absorption of oxirane rang due to epoxy group were admitted, but the absorption due to isocyanate group was not admitted at all.

Further, it was admitted that the polyamideepoxy resin of the formula (VI-3) was able to be dissolved in n-butanol in 40% or more and showed excellent solubility in general-purpose solvents having low boiling points. The 50% n-butanol solution of the polyamide-epoxy resin of the formula (VI-3) was stable at room temperature for 6 months or more without a large viscosity change and admitted to have an excellent pot life without any problems in practical use.

When the polyamide-epoxy resin of the formula (VI-3) was heat treated at 180° C. for 1 hour, it became insoluble in various organic solvents including N-methyl-2-pyrrolidone which is a polar solvent having great solubility, and was admitted to be self-cured due to three-dimensional crosslinking among molecules. The IR spectrum of this cured article showed disappearance of absorption of oxirane ring due to epoxy group at 915 cm$^{-1}$, and appearance of broad absorption at near 3400 cm$^{-1}$ due to the secondary hydroxyl group produced by addition reaction of epoxy group to the imino group produced by cleavage of amide bond as shown in the equation (XIV).

COMPARATIVE EXAMPLE 1

In the same reactor as used in Example 1, 146.5 g (0.778 mole) of m-xylene diisocyanate, 78.6 g (0.388 mole) of sebacic acid, and 1.12 g (0.008 mole) of sodium benzoate were placed in a nitrogen atmosphere and reacted in the same manner as described in Example 1 to yield an amide group-containing diisocyanate having isocyanate groups at both terminals. Then, the amide 10 group-containing diisocyanate was maintained at 160° C., followed by dropping of 174.3 g (0.778 mole) of ethylene glycol diglycidyl ether (Denacol EX-810, a trade name, mfd. by Nagase Chemicals, Ltd.) in 10 minutes. After reacting at 160° C. for 5 hours, a polyamide-epoxy resin of the following formula (VI-4) was obtained.

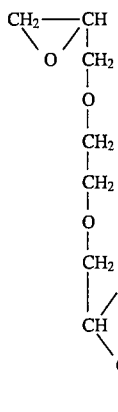
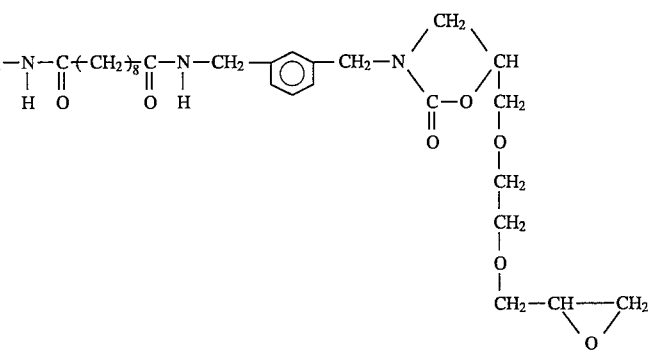

(VI-4)

IR spectrum of this polyamide-epoxy resin revealed the presence of absorption of carbonyl group due to the amide bond and ester bond of 2-oxazolidone ring as in Example 1, absorption of imino group due to amide bond, and absorption of oxirane ring due to epoxy group, but did not show the absorption due to isocyanate group at all.

Further, the polyamide-epoxy resin of the formula (VI-4) was soluble in N-methyl-2-pyrrolidone, but was not soluble in general-purpose solvents having low boiling points such as n-butanol, methyl ethyl ketone, n-butyl acetate, etc.

COMPARATIVE EXAMPLE 2

In a 100-ml separable flask equipped with a stirrer, a thermometer and a cooling condenser, 21.8 g (0.089 mole) of 1,3-bis(1-isocyanato-1-methylethyl)benzene and 9.03 g (0.045 mole) of sebacic acid were placed and heated to 130° C. During the temperature rise, the reaction system became a uniform molten state. Generation of $CO_2$ gas was admitted. After the temperature rise, the reaction was carried out at 130° C. for 2 hours and at 160° C. for 3 hours to yield an amide group-containing diisocynate compound. This amide group-containing diisocyanate compound was maintained at 160° C., followed by addition of a solution obtained by dissolving 66.81 g (0.179 mole) of epoxy resin (bisphenol A type, D. E. R. 331J, a trade name, mfd. by Dow Chemical Co., epoxy equivalent weight: 187) in 40 g of methyl isobutyl ketone. After the addition, the temperature of the reaction system was lowered to about 60° C. temporarily, but raised to 150° C. after 30 minutes. Then, the reaction was carried out at 150° C. for 3 hours to yield a resin solution for comparison.

IR spectrum of the resin solution for comparison immediately after the reaction revealed the absorption at 2260 $cm^{-1}$ due to isocyanate group of the amide group-containing diisocyanate compound, but the absorption due to isocyanate group disappeared when allowed to stand at room temperature for 3 days.

When the resulting resin solution was dried at 135° C. for 2 hours, the absorption due to the isocyanate group was re-appeared, but disappeared again when further allowed to stand at room temperature for 3 days. The recovery of isocyanate group at a high temperature (135° C.) and the disappearance of the isocyanate group at a low temperature (room temperature) suggest the presence of urethane bond which can be decomposed with heating in the resin for comparison. Further, it was also suggested that the resin for comparison contained a byproduct having urethane bonds formed by addition reaction of the isocyanate group of the amide group-containing diisocyanate to the secondary hydroxyl group of epoxy resin.

COMPARATIVE EXAMPLE 3

An amide group-containing diisocyanate was synthesized in the same manner as described in Comparative Example 2. This amide group-containing diisocyanate was maintained at 160° C., followed by addition of 13.2 g (0.089 mole) of phthalic anhydride. After reacting at 160° C. for 3 hours, the isocyanate groups of the amide group-containing diisocyanate were blocked. To the resulting compound in an amount of 9.75 g (0.0108 mole), 8.11 g (0.0217 mole) of the same epoxy resin as used in Comparative Example 2, and 2.15 g (0.0109 mole) of 4,4'-diaminodiphenylmethane as a curing agent for epoxy resin were added, followed by addition of 8.57 g of N,N-dimethylacetamide to prepare a uniform solution having a solid content of 70%.

The resulting solution was coated on a substrate using a bar coater to give a film thickness of about 24 µm, followed by drying at 80° C. for 10 minutes. Then, another substrate was laminated on the coated layer, followed by curing at 180° C. for 3 hours with heating to give a test piece for adhesiveness test.

When an aluminum foil was used as the substrate, the 90° peeling adhesiveness according to ASTM D 1876-61T was 2.5–6.8 N/25 mm at 23° C. with largely varied values.

When an untreated steel plate was used as the substrate, the tensile shear adhesiveness according to ASTM D 1002-64 was $9.5 \times 10^6$ $N/m^2$ at 23° C. When the surfaces of peeled test piece after the 90° peeling adhesiveness test were observed by the naked eye, remarkable phase separation was observed on the surfaces of cured article.

COMPARATIVE EXAMPLE 4

An epoxy resin (bisphenol A type, Epomik R 301, a trade name, mfd. by Mitsui Petrochemical Industries, Ltd.; epoxy equivalent weight 475) in an amount of 18.11 g (0.0191 mole) was mixed with 1.89 g (0.0095 mole) of 4,4'-diaminodiphenylmethane, followed by addition of 8.57 g of N,N-dimethylacetamide to prepare uniform solution having a solid content of 70%.

Using this solution, test pieces for adhesiveness test were prepared in the same manner as described in Comparative Example 3. Adhesive strength of the test pieces was measured in the same manner as described in Comparative Example 3. The 90° peeling adhesiveness was 1.1 N/25 mm at 23° C. and the tensile shear adhesiveness was $11.0 \times 10^6$ N/m² at 23° C.

EXAMPLE 3

The process of Example 1 was repeated except that the reaction of m-tetramethylxylene diisocyanate with sebacid acid was carried out in the absence of a catalyst at 130° C. for 2 hours and at 160° C. for 3 hours, and the reaction of the amide group-containing diisocyanate with ethylene glycol diglycidyl ether was carried out by dropping the ethylene glycol diglycidyl ether for about 30 minutes to the amide group-containing diisocyanate, followed by addition of 1.01 g (0.007 mole) of sodium benzoate and reaction at 160° C. for 8 hours.

The intermediate and the resulting product had the same structure as those of Example 1 when confirmed by IR spectra and ¹H-NMR spectra.

EXAMPLE 4

An amide group-containing epoxy resin of the formula (VI-5) was produced in the same manner as described in Example 3 except for using a solution obtained by dissolving 261.8 g (0.700 mole) of the same epoxy resin as used in Comparative Example 2 in place of the ethylene glycol diglycidyl ether in 190 g of methyl isobutyl ketone and adding this solution to the reaction system separately in 10 times, each in about 45 g, so as not to lower the reaction temperature below 130° C. The resulting reaction product was purified by washed well with deionized water to remove the catalyst, followed by drying at 135° C. for 2 hours.

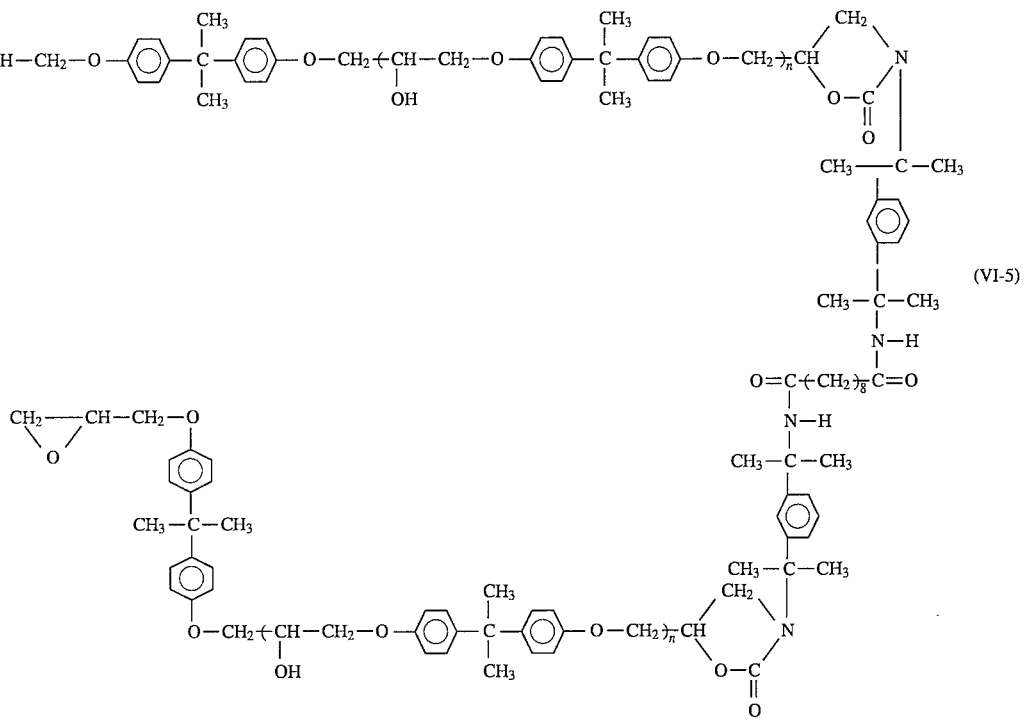

(VI-5)

In the formula (VI-5), n is 0, 1 or 2, and a plurality of n may be the same or different and an average value of n is about 0.14.

Figure 5:
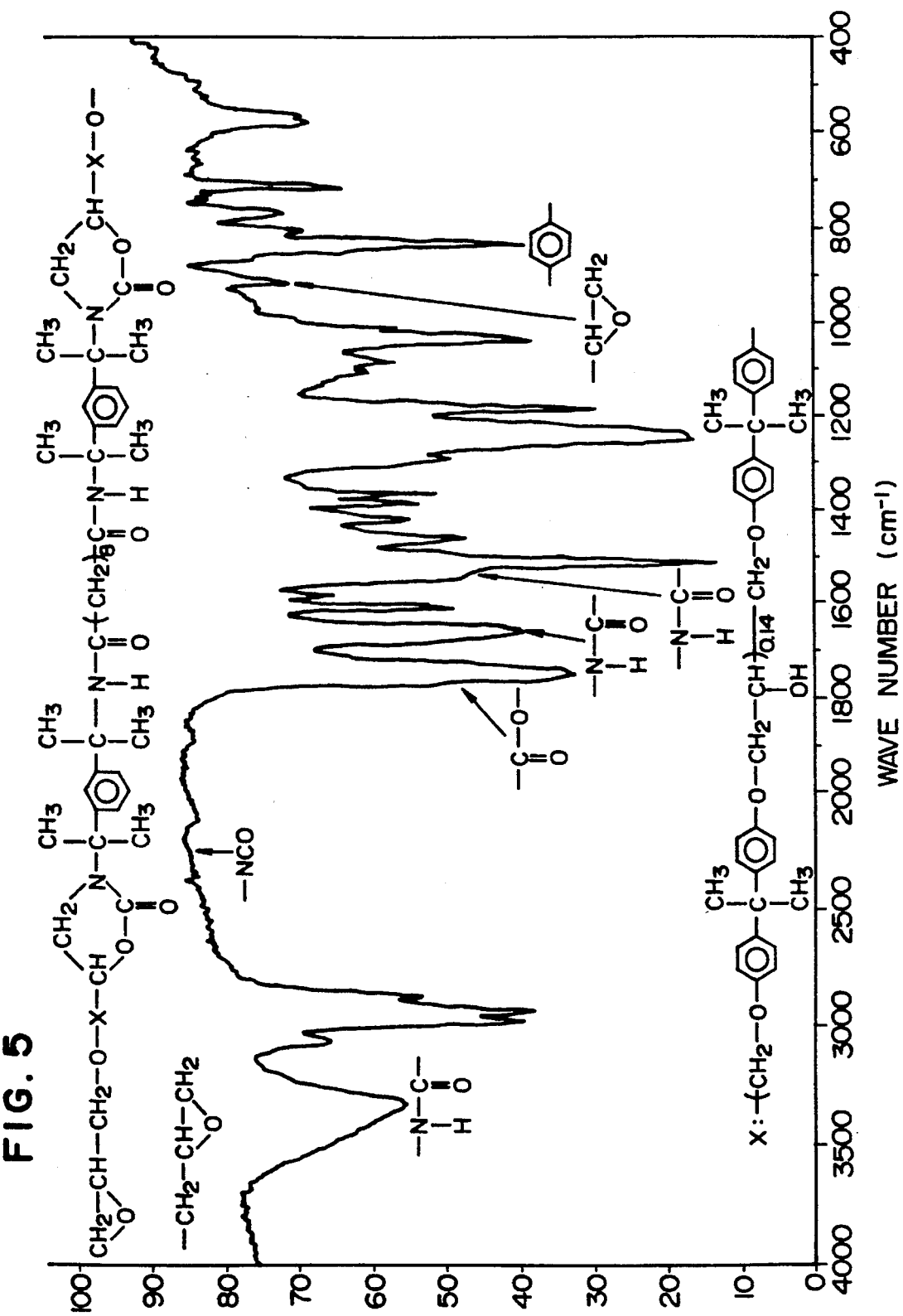
FIG. 5 is an IR spectrum of the amide group-containing epoxy resin obtained in Example 4.

The amide group-containing epoxy resin was subjected to measurement of IR spectrum, which is shown in FIG. 5. In FIG. 5, there are admitted the absorption of carbonyl group based on the amide bond at 1660 cm⁻¹, the absorption of imino group based on the amide bond at 3340 cm⁻¹ and 1540 cm⁻¹, and the absorption of oxirane ring due to epoxy group at 910 cm⁻¹. Further, the absorption of carbonyl group based on the ester bond of 2-oxazolidone ring appears at 1750 cm⁻¹, while the absorption at 2260 cm⁻¹ due to isocyanate group disappears. It was also admitted that the absorption intensity of epoxy group at 910 cm⁻¹ was reduced to about a half after the reaction compared with before the reaction based on the absorption intensity at 817 cm⁻¹ of aromatic ring based on the epoxy resin.

Figure 6:
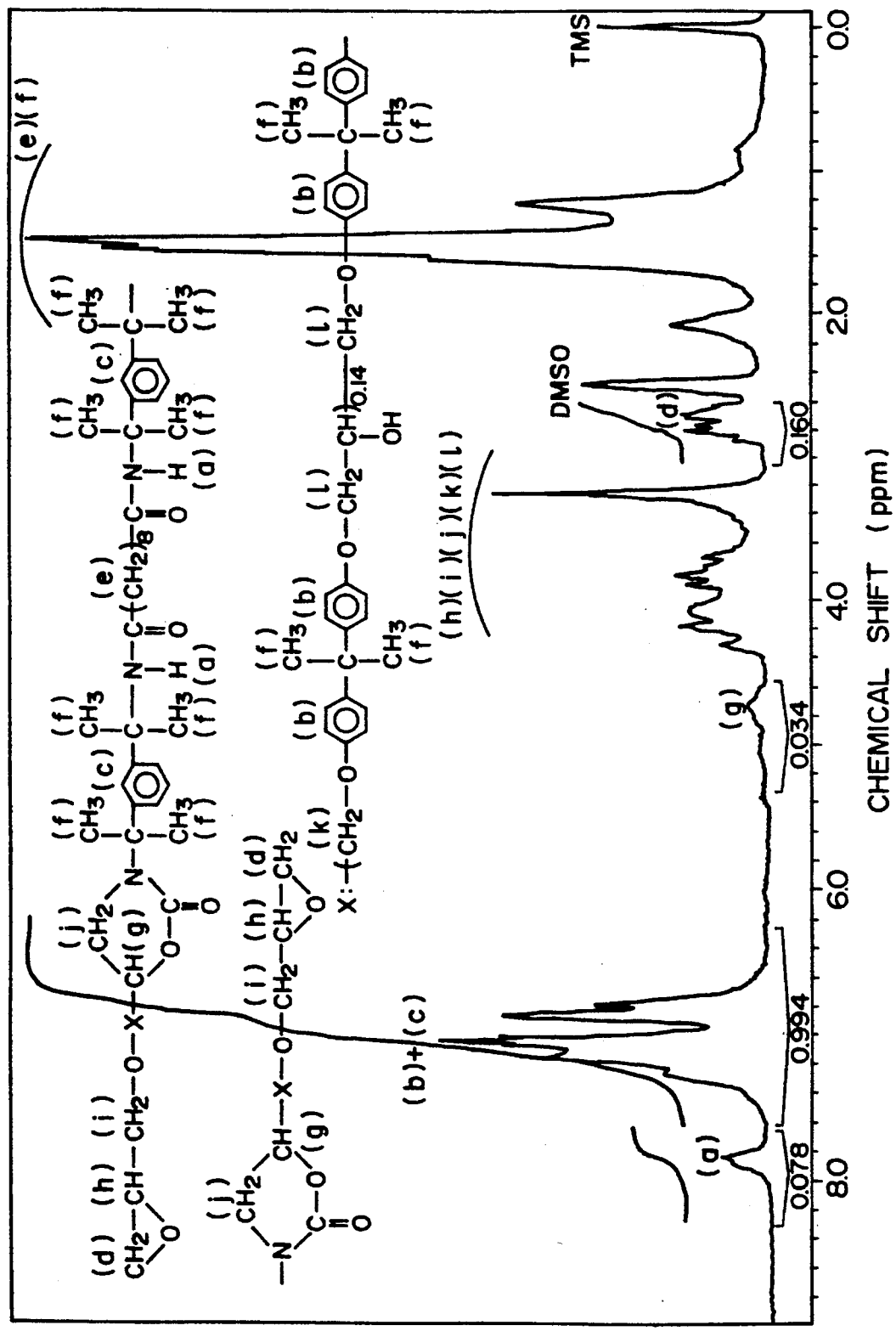
FIG. 6 is a $^1$H-NMR spectrum of the amide group-containing epoxy resin obtained in Example 4.

¹H-NMR spectrum of the amide group-containing epoxy resin is shown in FIG. 6, wherein the integrating intensity ratio is (a)/(b)+(c)/(d), the theoretical value is 1/13.1/2, and the measured value is 1/12.7/2.1. In FIG. 6, there are admitted peaks at 6.4–7.6 ppm due to proton of aromatic ring, at 7.6–8.1 ppm due to proton of imino group based on the amide bond, and at 2.6–3.0 ppm due to methylene group in the oxirane ring of epoxy group. It was admitted that the theoretical values and the measured values of the integrating intensity of these peaks were almost agreed.

EXAMPLE 5

In a 3-liter separable flask equipped with a stirrer, a thermometer and a cooling condenser, 513.0 g (2.100 moles) of 1,3-bis(1-isocyanato-1-methylethyl)benzene, and 212.36 g (1.05 moles) of sebacic acid were placed and reacted in the same manner as described in Example 3 to yield an amide group-containing diisocyanate.

The resulting amide group-containing diisocyanate was maintained at 160° C., followed by separate addition of a solution obtained by dissolving 1570.8 g (4.200 moles) of epoxy resin (bisphenol A type, D.E.R. 331J, a trade name, mfd. by Dow Chemical Co.; epoxy equivalent weight 187) in 400 g of methyl isobutyl ketone in 10 times, about 200 g in each time, so as not to lower the temperature of reaction system below 130° C. Then, the reaction was further carried out for 22 hours at that temperature until the isocyanate groups disappeared to yield a solution of amide group-containing epoxy resin with unreacted epoxy resin in about 36%. After washing well with xylene, the unreacted epoxy resin was dissolved and removed, followed by drying at 150° C. for 2 hours for purification.

The thus obtained amide group-containing epoxy resin in an amount of 18.63 g (0.0138 mole) was mixed with 1.37 g (0.0069 mole) of 4,4'-diaminodiphenylmethane, followed by addition of 8.57 g of N,N-dimethylacetamide to prepare a uniform solution having a solid content of 70%.

Using this solution, test pieces for adhesiveness test were prepared in the same manner as described in Comparative Example 3. Adhesive strength of the test pieces was measured in the same manner as described in Comparative Example 3. The 90° peeling adhesiveness was 21.8 N/25 mm at 23° C. and the tensile shear adhesiveness was $12.8 \times 10^6$ N/m$^2$ at 23° C.

EXAMPLE 6

In the same reactor as used in Example 5, 150.17 g (1,000 mole) of triethylene glycol, 200.14 g (2,000 moles) of succinic anhydride and 150 g of methyl isobutyl ketone were placed and heated to 130° C. During the temperature rise, the reaction system became a uniform solution. After the temperature rise, half esterification was carried out at 130° C. for 3 hours to yield a solution of dicarboxylic acid having two ester bonds.

After cooling the dicarboxylic acid solution to room temperature, 488.6 g (2.000 moles) of 1,3-bis(1-isocyanato-1-methylethyl)benzene was added thereto, followed by the same procedure as described in Example 3 to give an amide group-containing diisocyanate solution.

The resulting amide group-containing diisocyanate solution was maintained at 160° C., followed by separate addition of a solution obtained by dissolving 1496 g (4.000 moles) of epoxy resin (bisphenol A type, D.E.R. 331J, a trade name, mfd. by Dow Chemical Co.; epoxy equivalent weight 187) in 500 g of methyl isobutyl ketone in 10 times, about 200 g in each time, so as not to lower the temperature of reaction system below 130° C. Then, the reaction was further carried out for 18 hours at that temperature until the isocyanate groups disappeared to yield a solution of amide group-containing epoxy resin with unreacted epoxy resin in about 33%. After washing well with xylene, the unreacted epoxy resin was dissolved and removed, followed by drying at 150° C. for 2 hours for purification.

The thus obtained amide group-containing epoxy resin in an amount of 18.76 g (0.0125 mole) was mixed with 1.24 g (0.0063 mole) of 4,4'-diaminodiphenylmethane, followed by addition of 8.57 g of N,N-dimethylacetamide to prepare a uniform solution having a solid content of 70%.

Using this solution, test pieces for adhesiveness test were prepared in the same manner as described in Comparative Example 3. Adhesive strength of the test pieces was measured in the same manner as described in Comparative Example 3. The 90° peeling adhesiveness was 24.9 N/25 mm at 23° C. and the tensile shear adhesiveness was $12.7 \times 10^6$ N/m$^2$ at 23° C.

Evaluation results of adhesiveness of cured articles obtained in Examples 5 and 6 and Comparative Examples 3 and 4 are listed in Table 1.

TABLE 1

|  | Example No. | | Comparative Example No. | |
| --- | --- | --- | --- | --- |
|  | 5 | 6 | 3 | 4 |
| 90° peeling adhesiveness (N/25 mm) | 21.8 | 24.9 | 2.5–6.8 | 1.1 |
| Tensile shear adhesiveness ($\times 10^6$ N/m$^2$) | 12.8 | 12.7 | 9.5 | 11.0 |
| Peeled surface state of cured articles after 90° peeling adhesiveness test | Uniform | Uniform | Non-uniform (phase separation) | Uniform |

As is clear from Table 1, the amide group-containing epoxy resin of the present invention has high adhesiveness and good uniforming of cured articles not accomplished by the epoxy resins of Comparative Examples.

As mentioned above, since the amide group-containing epoxy resin of the present invention gives cured articles having high adhesiveness and good uniformity, it can be widely used as an adhesive, a coating composition, and the like.

What is claimed is:

1. An amide group-containing epoxy resin represented by the formula:

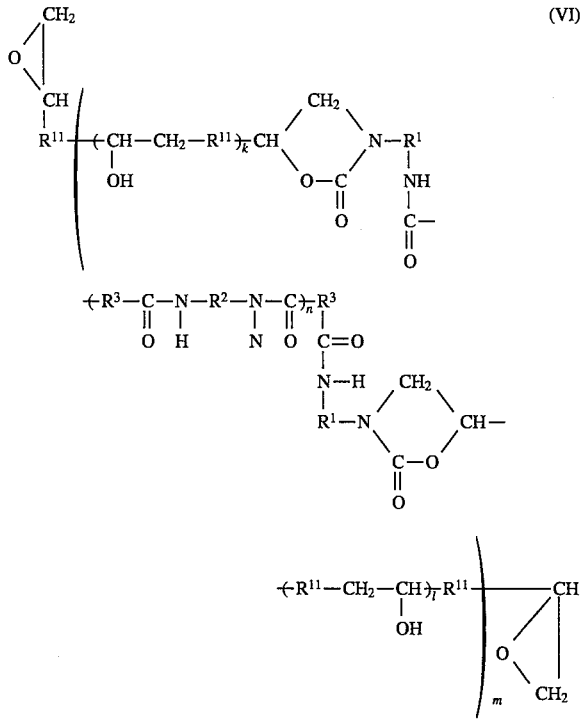

wherein $R^{11}$ is a divalent organic group, and a plurality of $R^{11}$ may be the same or different; $R^1$ is a group of the formula:

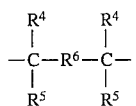

wherein $R^4$ is a hydrogen atom or a monovalent organic group; $R^5$ is a monovalent organic group; $R^6$ is a phenylene group or a naphthylene group; $R^2$ is a group of the formula:

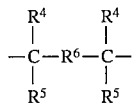

wherein $R^4$ is a hydrogen atom or a monovalent organic group; $R^5$ is a monovalent organic group; $R^6$ is a phenylene group or a naphthylene group; and $R^3$ is a divalent organic group, a plurality of $R^1$'s, $R^2$'s and $R^3$'s may be the same or different, respectively; n is zero or an integer of 1 or more; k is zero or an integer of 1 or more; l is zero or an integer of 1 or more; and m is an integer of 1 or more.

2. An amide group-containing epoxy resin according to claim 1, wherein said amide-group-containing epoxy resin is obtained by reacting an amide-group-containing diisocyanate compound of the formula:

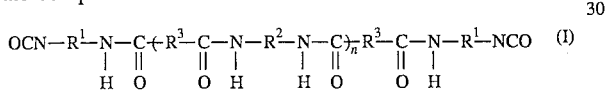

wherein $R^1$ is a group of the formula:

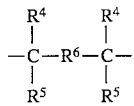

wherein $R^4$ is a hydrogen atom or a monovalent organic group; $R^5$ is a monovalent organic group; $R^6$ is a phenylene group or a naphthylene group; $R^2$ is a group of the formula:

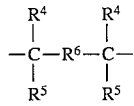

wherein $R^4$ is a hydrogen atom or a monovalent organic group; $R^5$ is a monovalent organic group; $R^6$ is a phenylene group or a naphthylene group; and $R^3$ is a divalent organic group, a plurality of $R^1$'s may be the same or different, and when a plurality of $R^2$'s and $R^3$'s are present, these may be the same or different; and n is zero or an integer of 1 or more; with an epoxy of the formula:

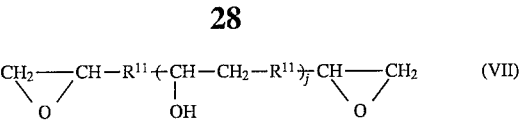

wherein $R^{11}$ is a divalent organic group; and j is zero or an integer of 1 or more.

3. An amide group-containing epoxy resin according to claim 2, wherein no byproduct having a urethane bond formed by addition reaction of an isocyanate group contained in the amide group-containing diisocyanate compound of the formula (I) with a secondary hydroxyl group contained in the epoxy resin of the formula (VII), is contained.

4. An amide group-containing epoxy resin according to claim 1, wherein $R^4$ is a methyl group; $R^5$ is a methyl group; and $R^6$ is a phenylene group.

5. An amide group-containing epoxy resin according to claim 4, wherein n is zero, and m is an integer of 1.

6. A process for producing an amide group-containing epoxy resin of claim 1, which comprises reacting an amide group-containing diisocyanate compound of the formula:

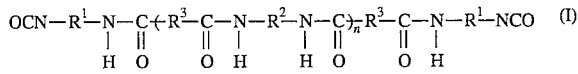

wherein $R^1$ is a group of the formula:

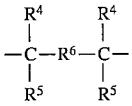

wherein $R^4$ is a hydrogen atom or a monovalent organic group; $R^5$ is a monovalent organic group; $R^6$ is a phenylene group or a naphthylene group; $R^2$ is a group of the formula:

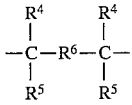

wherein $R^4$ is a hydrogen atom or a monovalent organic group; $R^5$ is a monovalent organic group; $R^6$ is a phenylene group or a naphthylene group; and $R^3$ is a divalent organic group, a plurality of $R^1$'s may be the same or different, and when a plurality of $R^2$'s and $R^3$'s are present, these may be the same or different; and n is zero or an integer of 1 or more; with an epoxy of the formula:

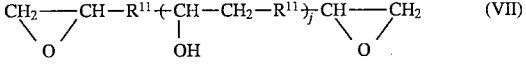

wherein $R^{11}$ is a divalent organic group; and j is zero or an integer of 1 or more, in a molar ratio of epoxy resin/diisocyanate of more than 1.

7. A process according to claim 6, wherein the reaction is carried out at a temperature of 80° C. or higher.

8. A polyamide-epoxy resin represented by the formula:

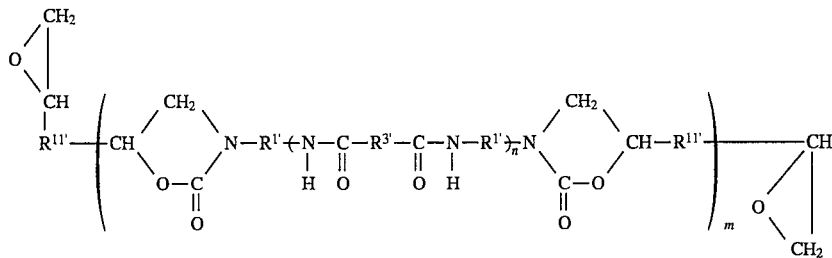

wherein $R^{1'}$ is a group of the formula:

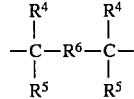

wherein $R^4$ is a hydrogen atom or a monovalent organic group; $R^5$ is a monovalent organic group; $R^6$ is a phenylene group or a naphthylene group; and $R^3$ is a divalent organic group, and when a plurality of $R^{1'}$'s and $R^{3'}$'s are present, these may be the same or different; $R^{11'}$ is a divalent organic group, and a plurality of $R^{11'}$'s may be the same or different; n is an integer of 1 or more; and m is an integer of 1 or more.

9. A polyamide-epoxy resin according to claim 8, wherein $R^{1'}$ is a group of the formula:

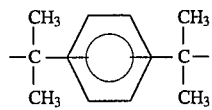

n is the formula (VI-1) is 1; and m in the formula (VI-1) is 1.

10. A process for producing a polyamide-epoxy resin of claim 8, which comprises reacting an amide group-containing diisocyanate compound represented by the formula:

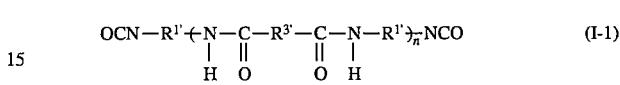

wherein $R^{1'}$ is a group of the formula:

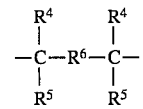

wherein $R^4$ is a hydrogen atom or a monovalent organic group; $R^5$ is a monovalent organic group; $R^6$ is a phenylene group or a naphthylene group; and $R^{3'}$ is a divalent organic group, and when a plurality of $R^{1'}$'s and $R^{3'}$'s are present, these may be the same or different; and n is an integer of 1 or more, with an epoxy compound of the formula:

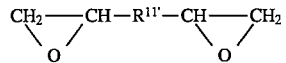

wherein $R^{11'}$ is a divalent organic group, in a molar ratio of epoxy compound/diisocyanate of more than 1.

11. A process according to claim 10, wherein the reaction is carried out at a temperature of 100° to 170° C. in the presence of a catalyst.

* * * * *